United States Patent [19]
Schehlmann et al.

[11] Patent Number: 6,124,274
[45] Date of Patent: Sep. 26, 2000

[54] USE OF ASCORBYL 2'-PHOSPHATES FOR STABILIZING VITAMIN A AND/OR VITAMIN A DERIVATIVES IN COSMETIC AND PHARMACEUTICAL PREPARATIONS

[75] Inventors: Volker Schehlmann, Römerberg; Horst Westenfelder, Neustadt, both of Germany

[73] Assignee: BASF Aktiengesellschaft, Ludwigshafen, Germany

[21] Appl. No.: 09/168,100

[22] Filed: Oct. 8, 1998

[30] Foreign Application Priority Data

Oct. 15, 1997 [DE] Germany ............... 197 45 506

[51] Int. Cl.⁷ ............... A61K 31/665; A61K 31/07

[52] U.S. Cl. ............... 514/99; 514/725
[58] Field of Search ............... 514/99, 725

[56] References Cited

FOREIGN PATENT DOCUMENTS

| 440398 | 8/1991 | European Pat. Off. . |
|---|---|---|
| 1489249 | 10/1967 | France . |
| 93/00085 | 1/1993 | WIPO . |

*Primary Examiner*—Raymond Henley, III
*Attorney, Agent, or Firm*—Keil & Weinkauf

[57] ABSTRACT

Ascorbyl 2'-phosphate is used for stabilizing vitamin A and/or vitamin A derivatives in cosmetic and pharmaceutical preparations.

5 Claims, No Drawings

USE OF ASCORBYL 2'-PHOSPHATES FOR STABILIZING VITAMIN A AND/OR VITAMIN A DERIVATIVES IN COSMETIC AND PHARMACEUTICAL PREPARATIONS

The use of ascorbyl 2'-phosphates for stabilizing vitamin A and/or vitamin A derivatives in cosmetic and pharmaceutical preparations

DESCRIPTION

The present invention relates to the use of ascorbyl 2'-phosphates for stabilizing vitamin A and/or vitamin A derivatives in cosmetic and pharmaceutical preparations.

Cosmetic and pharmaceutical products with vitamin A and/or vitamin A derivatives are becoming increasingly important in dermatology. Besides the treatment of acne, vitamin A and vitamin derivatives are very often employed in sunscreen compositions and products to counter photoaging.

Because of the low stability of vitamin A and derivatives to light and oxidation, demands made on cosmetic and pharmaceutical preparations with regard to the stabilization of vitamin A are great.

WO93/00085, which likewise describes the low stability of retinoids in skin protection compositions, discloses the use of both water- and fat-soluble antioxidants for stabilizing retinoids. The water-soluble stabilizers in this case are, inter alia, ascorbic acid and sulfur compounds such as sodium sulfite, sodium thiosulfite or thioglycerol. The fat-soluble antioxidants used include ascorbyl palmitate, butylated hydroxyanisole and α-tocopherol.

However, the abovementioned antioxidants have the disadvantage that either they are too unstable, like ascorbic acid or ascorbyl palmitate, or they may adversely affect the odor of the cosmetic or pharmaceutical product, like the thio compounds.

It is an object of the present invention to provide stabilizers of vitamin A or vitamin A derivatives for cosmetic and pharmaceutical preparations which do not have the abovementioned disadvantages.

We have found that this object is achieved by the use of ascorbyl 2'-phosphates, which distinctly improve the stability of vitamin A and/or vitamin A derivatives in cosmetic and pharmaceutical preparations.

Examples of vitamin A derivatives to be stabilized are all-E-retinoic acid (vitamin A acid), 9Z-retinoic acid, 13Z-retinoic acid, retinal, retinyl esters such as retinyl acetate or retinyl palmitate and mixtures thereof.

The ascorbyl 2'-phosphates according to the invention are preferably used to stabilize retinol (vitamin A alcohol) which is particularly sensitive to light and oxidation.

The stabilizing effect in this connection relates both to the odor and color and, in particular, to the active ingredient content of the preparation.

Thus, it has been possible to show that retinol-containing formulations, which are particularly prone to discoloration, were stable on storage both at room temperature and at 45° C. for at least 3 months in the presence of ascorbyl 2'-phosphates. Moreover both the retinol content and the content of ascorbyl 2'-phosphate remained constant throughout this period.

In order to achieve stabilization of vitamin A preparations, the ascorbyl 2'-phosphates are employed in a concentration of from 0.1 to 100000%, preferably 10 to 1000%, particularly preferably 50 to 200%, of the weight of vitamin A and/or vitamin A derivatives.

It is possible to use as ascorbyl 2'-phosphate both ascorbyl 2'-polyphosphate and, preferably, ascorbyl 2'-monophosphate and their salts. Particularly preferred stabilizers which should be mentioned in this connection are the sodium or magnesium salts of ascorbyl 2'-monophosphate.

The content of vitamin A in the cosmetic or pharmaceutical preparation is in the range from 0.01 to 10%, preferably in the range from 0.1 to 5%, particularly preferably in the range from 0.5 to 2%, of the total weight of the preparation.

The content of ascorbyl 2'-phosphate in the cosmetic or pharmaceutical formulation is in the range from 0.01 to 10%, preferably in the range from 0.1 to 5%, particularly preferably in the range from 0.5 to 2%, of the total weight of the preparation.

It is possible for the method according to the invention for stabilizing vitamin A and/or vitamin A derivatives in cosmetic and pharmaceutical preparations to add vitamin A and/or vitamin A derivatives and ascorbyl 2'-phosphate to the preparations either separately or else as ready-prepared mixture before, during or after the preparation thereof.

The nature of the carrier, ancillary substance or diluent determines whether the cosmetic or pharmaceutical preparation is a solution, an oil, a cream, an ointment, a lotion, a gel or a foam. Preparations of these types can be found, for example, in the journal "Seifen, Öle, Fette, Wachse", (1955) 147, and Hagers Handbuch der pharmazeutischen Praxis, Springer Verlag, Volume 2 (1991), Chapter 4.

Examples of cosmetic ancillary substances which are conventionally used and are suitable as additives are emulsifiers such as fatty alcohol ethoxylates, sorbitan fatty acid esters or lanolin derivatives, thickeners such as carboxymethylcellulose or crosslinked polyacrylic acid, preservatives and perfumes.

Examples of cosmetic oils are vegetable oils such as arachis oil, jojoba oil, olive oil, sesame oil, cottonseed oil, coconut oil, almond oil, grapeseed oil, castor oil or mineral oils, synthetic fatty acid esters and glycerides.

Examples of ointment bases are petrolatum, lanolin, Eucerin or polyethylene glycols.

Cream bases may be either emulsifiers of the water-in-oil type such as wool fat, sorbitan esters and monoglycerides, or oil-in-water emulsifiers such as sodium soaps, sodium salts of sulfuric esters of some fatty alcohols, or polysorbates.

The cosmetic preparation may contain organic solvents, preferably water-soluble organic solvents, for example lower aliphatic alcohols such as ethanol, propanol or isopropanol, glycols such as ethylene glycol, propylene glycol or their polyglycols, polyethylene glycol alkyl ethers of $C_1$–$C_4$-alcohols, simple or mixed ketones from $C_1$–$C_5$-alcohols such as acetone or methyl ethyl ketone, preferably glycols, polyglycols or polyethylene glycol alkyl ethers.

The cosmetic composition may also contain conventional cosmetic additives such as dyes, perfumes, surfactants, protein hydrolysates, superfatting agents, thickeners, luster agents, UV absorbers, herbal extracts, preservatives such as bactericidal or fungicidal substances, stabilizers such as magnesium or aluminum salts of fatty acids, complexing agents such as EDTA, antioxidants such as BHT, BHA, ascorbic acid or alpha-tocopherol.

The preparations comprising vitamin A and ascorbyl 2'-phosphate are suitable for protecting the skin for example against acne and for preventing photoaging.

The preparations can also be used for protecting the hair in hair cosmetics, for example in hair treatments, hair lotions, hair rinses, hair emulsions, treatment fluids for damaged ends, equalizing agents for permanent waves, hot oil treatment products, conditioners, setting lotions or hair sprays.

The following examples illustrate the cosmetic and pharmaceutical preparations in detail.

EXAMPLE 1

Oil-in-Water Cream

Content (% by weight)

| | |
|---|---|
| 2.0 | Ceteareth-6 |
| 2.0 | Ceteareth-25 |
| 10.0 | Mineral oil |
| 3.0 | Buxus Chinensis |
| 4.0 | Caprylic/capric triglycerides |
| 5.0 | petrolatum |
| 3.0 | Cetyl stearyl alcohol |
| 0.5 | Parabens |
| 1.0 | Sodium ascorbyl 2'-monophosphate |
| 5.0 | Propylene glycol |
| 0.2 | EDTA |
| 0.3 | Imidazolidinylurea |
| 0.1 | Tocopherol |
| 0.5 | Tocopheryl acetate |
| 1.0 | Retinol 10 CM (= 10% by weight retinol in caprylic/capric triglycerides) |
| ad 100 | water |

EXAMPLE 2

Water-in-Oil Cream

Content (% by weight)

| | |
|---|---|
| 6.0 | PEG-7 Hydrogenated castor oil |
| 10.0 | Mineral oil |
| 5.0 | Buxus Chinensis |
| 5.0 | Caprylic/capric triglycerides |
| 3.0 | petrolatum |
| 1.0 | Quaternium-18 bentonite |
| 0.5 | Parabens |
| 1.0 | Sodium ascorbyl 2'-monophosphate |
| 3.0 | 1,2-Propylene glycol |
| 0.1 | EDTA |
| 0.3 | Imidazolidinylurea |
| 0.2 | Tocopherol |
| 1.0 | Tocopheryl acetate |
| 1.0 | Retinol 10 CM (= 10% by weight retinol in caprylic/capric triglycerides) |
| ad 100 | Water |

EXAMPLE 3

Foam Setting Composition

Content (% by weight)

| | |
|---|---|
| 2.0 | Cocotrimonium methosulfate |
| 0.3 | Fragrance |
| 10.0 | Polyquaternium-46 |
| 2.0 | Polyquaternium-11 |
| 0.2 | Ceteareth-25 |
| 0.1 | Retinol 10 CM (= 10% by weight retinol in caprylic/capric triglycerides) |
| 1.0 | Sodium ascorbyl 2'-monophosphate |
| 1.0 | Panthenol USP |
| 15.0 | Ethanol |
| 10.0 | Propane/butane |
| ad 100 | Water |

EXAMPLE 4

Water-in-Oil Cream

Content (% by weight)

| | |
|---|---|
| 3.0 | Polyglyceryl-3 dioleate |
| 0.3 | PEG-40 Hydrogenated castor oil |
| 2.0 | Beeswax |
| 8.0 | Buxus Chinensis |
| 8.0 | Mineral oil |
| 5.0 | Cetearyl octanoate |
| 3.0 | Hydroxyoctacosanyl hydroxystearate |
| 3.0 | PEG-45 Dodecyl glycol copolymer |
| 1.0 | Panthenol |
| 0.1 | EDTA |
| 5.0 | Glycerol |
| 0.3 | Imidazolidinylurea |
| 0.8 | Sodium ascorbyl 2'-monophosphate |
| 1.0 | Tocopheryl acetate |
| 0.1 | Tocopherol |
| 0.2 | Bisabolol |
| 1.0 | Retinol 10 CM (= 10% by weight retinol in caprylic/capric triglycerides) |
| 0.2 | Methyldibromoglutaronitrile |
| ad 100 | Water |

EXAMPLE 5

Investigation of the storage stability of the vitamin A cream of Example 4

3 samples of the cream to be investigated were each stored separately at 6° C., 25° C. and 45° C. for up to 3 months. After 6 weeks and 3 months, each sample was investigated by HPLC for its retinol and sodium ascorbyl 2'-monophosphate contents. As shown by the results in Table 1, both the retinol and the sodium ascorbyl 2'-monophosphate contents remained constant throughout the investigation period.

Nor did the formulation become yellow in any of the three cases.

TABLE 1

| | Retinol content [% by weight] | Na ASMP*) content [% by weight] |
|---|---|---|
| Initial t = 0 | 0.1 (25° C.) | 0.78 (25° C.) |
| t = 6 weeks | 0.08 (6° C.) | 0.76 (6° C.) |
| | 0.10 (25° C.) | 0.80 (25° C.) |
| | 0.10 (45° C.) | 0.81 (45° C.) |
| t = 3 months | 0.08 (6° C.) | 0.74 (6° C.) |
| | 0.09 (25° C.) | 0.79 (25° C.) |
| | 0.08 (45° C.) | 0.77 (45° C.) |

*)Sodium ascorbyl 2'-monophosphate

We claim:

1. A method of stabilizing vitamin A and/or vitamin A derivatives in cosmetic and pharmaceutical preparations, which comprises combining vitamin A and/or vitamin A derivatives with ascorbyl 2'-phosphate.

2. A method as defined in claim 1, wherein ascorbyl 2'-phosphate is used in concentrations of from 0.1 to 100000% of the weight of vitamin A and/or vitamin A derivatives.

3. A method as defined in claims 1, wherein vitamin A and/or vitamin A derivatives are combined with sodium or magnesium salts of ascorbyl 2'-monophosphate.

4. A method as defined in claim 2 wherein ascorbyl 2'-phosphate is used in concentrations of from 50 to 200% of the weight of vitamin A and/or vitamin A derivatives.

5. A method as defined in claim 4, wherein vitamin A and/or vitamin A derivatives are combined with sodium or magnesium salts of ascorbyl 2-monophosphate.

* * * * *